(12) United States Patent
Mora Lopez et al.

(10) Patent No.: US 10,044,325 B2
(45) Date of Patent: Aug. 7, 2018

(54) SMALL SIGNAL AMPLIFIER

(71) Applicant: IMEC VZW, Leuven (BE)

(72) Inventors: Carolina Mora Lopez, Heverlee (BE); Srinjoy Mitra, Edinburg (GB)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/380,021

(22) Filed: Dec. 15, 2016

(65) Prior Publication Data
US 2017/0179891 A1    Jun. 22, 2017

(30) Foreign Application Priority Data

Dec. 16, 2015 (EP) ..................................... 15200499

(51) Int. Cl.
*H03F 3/45* (2006.01)
*H03F 1/26* (2006.01)
*A61B 5/04* (2006.01)

(52) U.S. Cl.
CPC ........... *H03F 1/26* (2013.01); *A61B 5/04001* (2013.01); *H03F 3/45475* (2013.01); *H03F 3/45179* (2013.01); *H03F 3/45183* (2013.01); *H03F 3/45188* (2013.01); *H03F 3/45192* (2013.01); *H03F 2200/171* (2013.01); *H03F 2200/261* (2013.01)

(58) Field of Classification Search
CPC .... H03F 3/45; H03F 3/45179; H03F 3/45183; H03F 3/45188; H03F 1/307; H03F 3/30; H03F 3/3001; H03F 3/3022
USPC ................................. 330/253, 255
See application file for complete search history.

(56) References Cited

U.S. PATENT DOCUMENTS

| | | | |
|---|---|---|---|
| 6,642,543 B1 | 11/2003 | El Gamal et al. | |
| 7,109,794 B2 * | 9/2006 | Killat | H03F 3/45183 330/253 |
| 7,119,600 B2 * | 10/2006 | Chen | H03K 19/018528 330/253 |

(Continued)

FOREIGN PATENT DOCUMENTS

GB    2 412 259 A    9/2005

OTHER PUBLICATIONS

European Search Report, European Patent Application No. 15200499.0, dated Jun. 14, 2016, 9 pages.

(Continued)

*Primary Examiner* — Khanh V Nguyen
(74) *Attorney, Agent, or Firm* — McDonnell Boehnen Hulbert & Berghoff LLP

(57) ABSTRACT

An amplifier circuit, a voltage sensing apparatus, and an amplification method are disclosed. The amplifier circuit comprises (1) an input stage comprising a first set of transistors to which an input signal to be amplified is applied, the transistors of the first set comprising a semiconductor body, and (2) a processing stage comprising a second set of transistors for processing the signal from the input stage and generating an output signal. The transistors of the first set have a thicker gate oxide than the transistors of the second set, and are therefore suitable for higher voltage operation. The first and second sets of transistors are supplied by the same voltage supply of the amplifier circuit. The semiconductor body of the first set of transistors is connected to a reference potential to lower the threshold voltage.

18 Claims, 2 Drawing Sheets

(56) References Cited

U.S. PATENT DOCUMENTS

| | | | | |
|---|---|---|---|---|
| 7,271,651 | B2* | 9/2007 | Chen | H03F 3/45183 |
| | | | | 330/253 |
| 7,683,714 | B2* | 3/2010 | Nishimura | H03F 3/3022 |
| | | | | 330/253 |
| 7,944,299 | B2* | 5/2011 | Mangudi | G05F 3/205 |
| | | | | 327/534 |
| 8,928,406 | B2* | 1/2015 | Albinet | H03F 3/45636 |
| | | | | 330/253 |
| 2006/0290426 | A1 | 12/2006 | Chen et al. | |
| 2011/0001561 | A1 | 1/2011 | Ouchi | |
| 2014/0180052 | A1 | 6/2014 | Lo et al. | |

OTHER PUBLICATIONS

Chatterjee, Shouri et al., "0.5-V Analog Circuit Techniques and Their Application in OTA and Filter Design", IEEE Journal of Solid-State Circuits, vol. 40, No. 12, Dec. 2005, pp. 2373-2387.
Lehmann, Torsten et al., "Ultra-Low Voltage CMOS Cascade Amplifier", Proceedings of the 26th Solid-State Circuits Conference, Sep. 19-21, 2000, pp. 3-6.

* cited by examiner

SMALL SIGNAL AMPLIFIER

CROSS-REFERENCE TO RELATED APPLICATIONS

The present application is a non-provisional patent application claiming priority to European Patent Application No. EP 15200499.0, filed Dec. 16, 2015, the contents of which are hereby incorporated by reference.

FIELD OF THE DISCLOSURE

This disclosure relates to the field of signal amplification, in particular small signal amplification, for which the characteristics of the individual components of the amplifier circuit have an impact on the signal to noise performance of the amplifier circuit. One example is signal amplification of biological signals, for example biopotential signals.

BACKGROUND

There are numerous situations in which a small signal needs to be measured and amplified. Sensors for monitoring biosignals (potentials or currents) are one example. Voltage sensing apparatuses for bio-sensing purposes have an important role in the areas of diagnostic analysis of tissue and neuroscience experimentation. Known biosensors comprising small signal voltage sensing apparatus include, for example, neural probes, alternatively named deep-brain implants, or flexible electrode arrays.

Embodiments disclosed herein may be described in connection with one possible use for biopotential measurement. Such biosensors may be used, for example, to measure neural activity at one or more areas of a brain or cardiac activity at one or more areas of a heart. Typically, biopotential sensing apparatuses comprise at least one electrode adapted to detect a voltage present in biological tissue proximate to the electrode.

Measuring circuitry suitable for recording biopotentials is often connected to at least one electrode by a respective connecting wire. Such measuring circuitry may further comprise processing circuitry, for example, a filter or digitization circuitry.

Amplifier circuits are typically implemented as transistor circuits, using one particular transistor technology type. Such technology types typically include standard transistors for operation at core voltages such as 1.2V and high voltage transistors which have thicker gate oxides, for operation at higher voltages such as 3.3V. The standard transistors in scaled technologies have large gate leakage currents that cause high shot noise. This noise can be prohibitive in low frequency analog applications that require very low noise performance. Gate leakage can also cause other issues in an amplifier input stage such as reduced input impedance since excessive current will flow to the input nodes.

US 2006/0290426 discloses a circuit with an input stage implemented using thick gate oxide transistors and a second stage using thin gate oxide transistors. The problem with such a circuit is that the input voltage range which can be processed by the circuit is reduced. In particular, there is a mismatch between the characteristics of the thin and thick gate oxide transistors.

There is therefore a need for an amplifier circuit which can address the issues of gate leakage so that improved signal to noise performance can be achieved, while enabling processing of an input signal over a wide voltage range.

SUMMARY

According to an aspect of this disclosure, there is provided an amplifier circuit comprising: an input stage comprising a first set of transistors to which an input signal to be amplified is applied, the transistors of the first set comprising a semiconductor body; and a processing stage comprising a second set of transistors for processing the signal from the input stage and generating an output signal, wherein the transistors of the first set have a thicker gate oxide than the transistors of the second set, and are therefore suitable for higher voltage operation, and wherein the first and second sets of transistors are supplied by the same voltage supply of the amplifier circuit, and wherein the semiconductor body of the first set of transistors is connected to a reference potential thereby to lower the threshold voltage.

By using thick-oxide transistors in the critical nodes and standard transistors in the non-critical nodes, the problems of gate leakage are addressed. The thick oxide transistors, however, exhibit high threshold voltage behavior. To enable the combination and correct biasing of both high threshold voltage thick oxide transistors and standard transistors while using a low supply voltage, forward body biasing of the thick oxide transistors is used to lower their threshold voltage while ensuring low junction-diode forward current.

The amplifier circuit may comprise a differential amplifier, wherein the input stage comprises a first input transistor, wherein the first differential input is provided to the gate of the first input transistor, and a second input transistor, wherein the second differential input is provided to the gate of the second input transistor.

The input transistors contribute most to the overall noise of the amplifier, so that the use of thick gate oxide transistors improves the overall noise performance. It enables a high input impedance to be provided, thereby limiting leakage currents from the inputs.

The voltage supply of the amplifier circuit is for example less than 2V. By way of example, the voltage supply may be 1.2V, whereas the thick gate oxide transistors are designed for operation at voltage above 2V, for example 3.3V.

The reference potential is in the range 0.3V to 1V. The reference potential used as a semiconductor bulk bias is for example 0.6V.

According to an exemplary embodiment, the voltage sensing apparatus comprises: an electrode comprising an exposed, electrically conductive, surface area; and an amplifier circuit as claimed in any preceding claim for receiving the electrode potential as an input signal.

According to an exemplary embodiment, the amplifier circuit comprises an instrumentation amplifier with a high-pass filter connected in a feedback path.

Examples in accordance with another aspect of the disclosure provide an amplification method, comprising: processing an input signal using an input stage comprising a first set of transistors, the transistors of the first set comprising a semiconductor body; processing the signal from the input stage and generating an output signal using a processing stage comprising a second set of transistors, wherein the transistors of the first set have a thicker gate oxide than the transistors of the second set, and are therefore suitable for higher voltage operation; supplying the first and second sets of transistors by the same voltage supply of the amplifier circuit, and connecting the semiconductor body of the first set of transistors to a reference potential thereby to lower the threshold voltage.

The method may comprise processing a differential input signal by providing a first differential input to the gate of a first input transistor of the input stage, and providing a second differential to the gate of a second input transistor of the input stage.

The amplifier circuit may be provided with a voltage supply of less than 2V and the reference potential may be in the range 0.3V to 1V, for example 0.6V.

BRIEF DESCRIPTION OF THE FIGURES

Examples embodiments will now be described in detail, with reference to the accompanying drawings, in which.

DETAILED DESCRIPTION

Some embodiments provide an amplifier circuit comprising an input stage comprising a first set of transistors to which an input signal to be amplified is applied, the transistors of the first set comprising a semiconductor body, and a processing stage comprising a second set of transistors for processing the signal from the input stage and generating an output signal.

The transistors of the first set have a thicker gate oxide than the transistors of the second set, and may therefore be suitable for higher voltage operation, and the first and second sets of transistors are supplied by the same voltage supply of the amplifier circuit. This reduces the effect of gate leakage currents. The semiconductor body of the first set of transistors is connected to a reference potential thereby to lower the threshold voltage. This enables the circuit to process a wider range of input signals.

Some embodiments are applicable to the amplification of small signals generally, by which is meant signals for which the signal to noise ratio is low, for example such that leakage currents in the amplifier circuit are significant.

Figure 1:
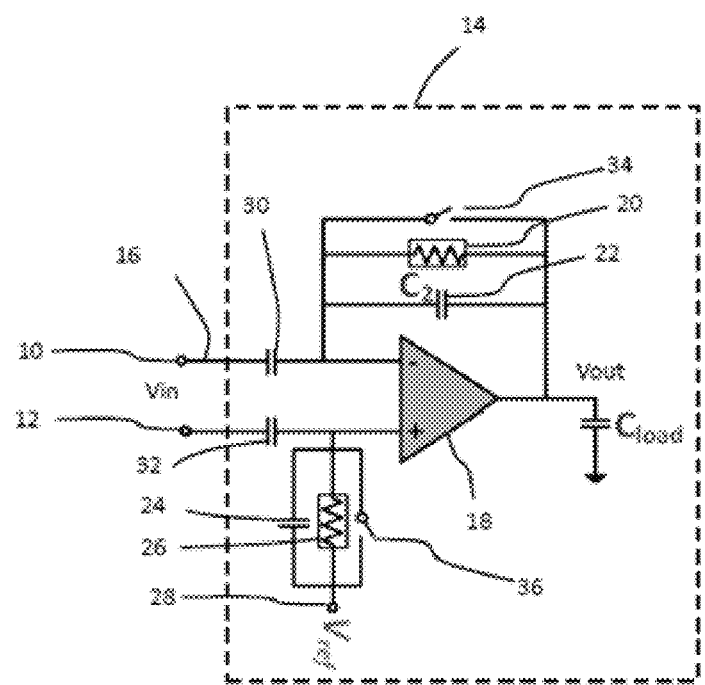
FIG. 1 illustrates a schematic of an electrical circuit for a portion of a biopotential measurement system.

FIG. 1 shows a representative schematic of a portion of a voltage sensing apparatus. Specifically, there is identified a biopotential sensing electrode 10 and a reference electrode 12 connected to an instrumentation amplifier 14 by a connecting wire 16.

The sensing electrode 10 comprises an electrically conductive contact (for example, a metal electrode) that, in use, is in contact with, for example, a portion of tissue being examined so as to measure a voltage present in or at the said tissue. This measured input voltage $V_{in}$ is subsequently passed to the instrumentation amplifier, which functions as sensing circuitry.

The sensing electrode 10 may for example be positioned on the exterior surface of a shank of a neural probe.

The reference electrode 12 may have the same structure as the sensing electrode 10 and can have the same surface area as the sensing electrode or it can be larger. The voltage at the input $V_{in}$ varies according to a varying voltage level at the tissue being examined.

The instrumentation amplifier comprises an operational transconductance amplifier 18 having a negative feedback loop in which a high pass filter 20, 22 is provided. The amplifier generates an output voltage $V_{out}$. The high pass filter is embodied as a standard passive first-order high pass filter having a filter capacitor 22 and a filter resistor 20 (in practice implemented as a transistor) connected between the output node of the amplifier and the inverting input. Provision of the high pass filter may permit reduction of the very low frequency artifacts (i.e. low frequency noise or DC biasing) that may saturate the instrumentation amplifier, for example the operational transconductance amplifier 18.

Another high pass filter 24, 26 is disposed at the reference input of the instrumentation amplifier. This filter is connected at one end 28 to a filter node held at a reference voltage level $V_{ref}$ to bias the circuit at a proper DC point.

In embodiments the capacitances of the filter capacitors 22 and 24 are very small (e.g., ~5 pF), but the resistances of the filter resistors 20 and 26 are sufficiently large (e.g., >1 GΩ) so as to achieve a relatively low corner frequency of the high-pass filter. In one example, this corner frequency is less than 10 Hz, in other examples, the corner frequency of the high pass filter is less than 1 Hz.

In some embodiments, the output signal from the instrumentation amplifier 14 is derived from the potential generated at the sensing electrode 10 and the reference electrode 12.

The amplifier has two input capacitors 30, 32 which are used to reject DC offsets present at the sensing electrode 10 and the reference electrode 12. This prevents the saturation of the instrumentation amplifier when exposed to large DC offset at the input.

The gain of the instrumentation amplifier is given by the ratio of the input capacitor 30 and the feedback capacitor 22.

By way of example, the gain A of the instrumentation amplifier may be adjusted to be no less than 1. It may be much greater than 1, such as 50 or more or, for example, 100 or more. A higher gain value (for example, greater than 50) may reduce the performance constraint of optional subsequent amplification stages.

Two reset switches 34,36 are connected across the plates of the capacitors 22, 24. They reset the circuit, bringing the output voltage to a reference voltage; that is bringing the capacitor back to a 'zero initial conditions' state.

Figure 2A:
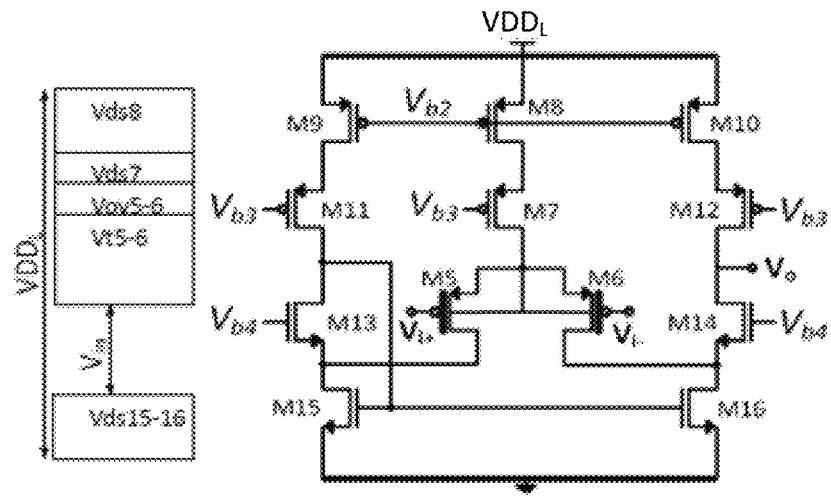
FIG. 2A depicts a first example of amplifier circuit.
Figure 2B:
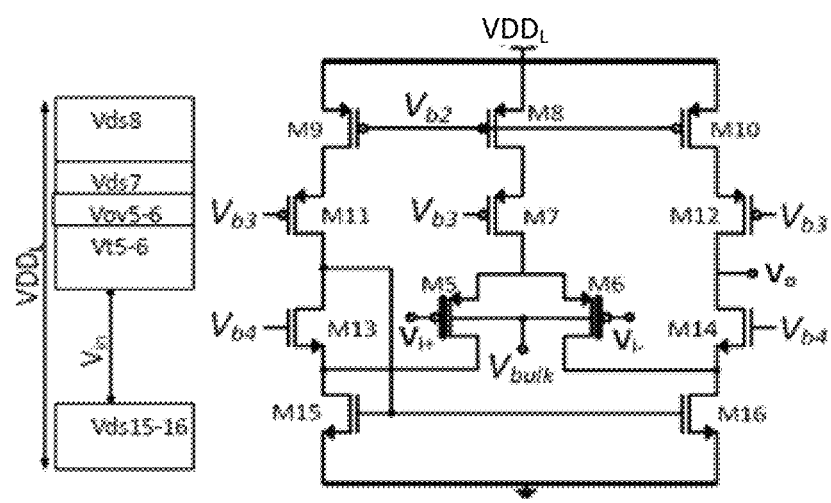
FIG. 2B depicts a second example of amplifier circuit.

FIGS. 2A and 2B show two examples of the circuit for the operational transconductance amplifier 18 in FIG. 1. The approach of embodiments of the present disclosure is applied in the circuit of FIG. 2B in that a connection to the bulk potential is used instead of a connection to the source node.

The transistors are for example bulk CMOS transistors, and may have a bulk semiconductor epi-layer which may be p-type or n-type, and into which implantation wells are formed. For example there may be a p-type substrate in which n-type devices are formed, as well as n-type wells in which p-type devices are formed. A silicon on insulator structure may similarly have a bulk silicon layer.

In both circuits, there is provided a folded cascode operational transconductance amplifier (OTA). The circuit comprises a pair of p-type input transistors M5, M6 which draw a current from a bias circuit comprising two p-type transistors M7, M8 in series which have respective bias voltages Vb2, Vb3 applied to their gates. The current is shared between the differential inputs in dependence on the signal levels at the inputs. The voltages Vb2 and Vb3 are generated by any standard biasing circuit (for example a cascade current mirror).

The two outer branches of the amplifier have the same current driven through them from respective current mirror transistors M9, M10 so that the current is mirrored in all three branches.

The outer branches each comprise two cascode transistors M11, M13 in the left branch and M12, M14 in the right branch. These transistors have bias voltages Vb3 and Vb4 applied to their gates. The currents are combined through the transistors M15 and M16.

This is just one known example of operational transconductance amplifier, and there are numerous possible variations.

The transistors M5 and M6 are thicker gate oxide transistors designed for operation at voltages above the supply voltage $VDD_L$ which is for example less than 2V, for example in the range 1.1V-1.3V.

The chart to the left in FIGS. 2A and 2B shows the voltage drops across the various transistor devices in series from the ground potential to the $VDD_L$ potential, namely the drain source voltage of M15 and M16 (Vds15-16), the drain source voltage of the transistors M5 and M6, shown separately as the threshold voltage (Vt5-6) and the overdrive voltage (Vov5-6), the drain source voltage of the transistor M7 (Vds7) and the drain source voltage of the transistor M8 (Vds8).

In the circuit of FIG. 2A, the bulk of the transistors M5 and M6 is connected to the source.

Some embodiments are based on the recognition that the use of thick oxide layer transistors reduces the range of input voltages which may be processed before the circuit reaches saturation. Some embodiments are based on the recognition that in many circuit architectures, the larger threshold voltage of the thick gate oxide transistors results in a reduction of the window of input signals that may be amplified. In the circuit of FIG. 2B, the bulk of the transistors M5 and M6 is connected to a reference bulk voltage Vbulk.

The bulk voltage is for example in the range 0.3V to 1V, for example 0.6V.

As shown in the chart in FIG. 2B, the threshold voltage Vt5-6 of the transistors M5 and M6 is reduced so that the range of input voltage which can be processed (without clipping) is increased.

Due to the high gate leakage of standard transistors, the input transistors M5 and M6 of the amplifier are implemented with thick oxide transistors. In an overall circuit making use of the instrumentation amplifier, all transistors which process a voltage directly from the input source may be implemented as thick gate oxide transistors and all others may be implemented as standard transistors.

This may eliminate gate shot-noise components and minimizes the current flowing through the resistors 20, 26, thus keeping the input-node voltages and the high-pass corner frequency stable. To enable the combination and correct biasing of both high threshold voltage thick oxide and standard transistors (M7-M16 in FIG. 2), the forward body biasing of the input transistors M5, M6 lowers their threshold voltage while ensuring low junction-diode forward current.

Some embodiments may be applied to wideband or narrowband amplifiers, with fixed or variable gain. The amplifier may be single ended or differential, and it may or may not include common-mode feedback. The amplifier is of general applicability to small signal amplification, such as biopotential signal amplification generally as well as other small signal amplifier applications.

Various other modifications will be readily apparent to those skilled in the art. For example, a skilled person would be able to substitute the above embodied P channel MOSFET transistor with other suitable transducers (e.g., an N channel MOSFET transistor, an FET and/or a PNP/NPN transistor) without departing from the scope the present disclosure. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

What is claimed is:

1. An amplifier circuit comprising:
    an input stage comprising a first set of transistors to which an input signal to be amplified is applied, the transistors of the first set comprising a semiconductor body; and
    a processing stage comprising a second set of transistors for processing the signal from the input stage and generating an output signal,
    wherein the transistors of the first set have a thicker gate oxide than the transistors of the second set, and wherein the transistors of the first set are therefore suitable for higher voltage operation, and wherein the first and second sets of transistors are supplied by a same voltage supply of the amplifier circuit, and
    wherein the semiconductor body of the first set of transistors is connected to a reference potential so as to lower a threshold voltage of the first set of transistors, wherein the reference potential is connected to a reference input of the input stage via a high-pass filter.

2. The amplifier circuit of claim 1, wherein the input stage comprises a differential amplifier, and wherein the first set of transistors comprises:
    a first input transistor, wherein a first differential input is provided to a gate of the first input transistor; and
    a second input transistor, wherein a second differential input is provided to a gate of the second input transistor.

3. The amplifier circuit of claim 1, wherein the voltage supply of the amplifier circuit is less than 2V.

4. The amplifier circuit of claim 1, wherein the reference potential is in a range from 0.3V to 1V.

5. The amplifier circuit of claim 1, wherein the voltage supply of the amplifier circuit and the reference potential are different.

6. A voltage sensing apparatus for detecting a voltage of biological tissue, the voltage sensing apparatus comprising:
    an electrode configured to measure a voltage from a portion of tissue, wherein the electrode comprises an exposed, electrically conductive, surface area; and
    an amplifier circuit for receiving an electrode potential from the electrode as an input signal, the amplifier circuit comprising:
        an input stage comprising a first set of transistors to which an input signal to be amplified is applied, the transistors of the first set comprising a semiconductor body; and
        a processing stage comprising a second set of transistors for processing the signal from the input stage and generating an output signal,
        wherein the transistors of the first set have a thicker gate oxide than the transistors of the second set, and wherein the transistors of the first set are suitable for higher voltage operation than the transistors of the second set, and wherein the first and second sets of transistors are supplied by a same voltage supply of the amplifier circuit, and
        wherein the semiconductor body of the first set of transistors is connected to a reference potential so as to lower a threshold voltage of the first set of transistors.

7. The voltage sensing apparatus of claim 6, wherein the amplifier circuit comprises an instrumentation amplifier with a high-pass filter connected in a feedback path.

8. The voltage sensing apparatus of claim 6, wherein the input stage comprises a differential amplifier, and wherein the first set of transistors comprises:

a first input transistor, wherein a first differential input is provided to a gate of the first input transistor; and a second input transistor, wherein a second differential input is provided to a gate of the second input transistor.

9. The voltage sensing apparatus of claim 6, wherein the voltage supply of the amplifier circuit is less than 2V.

10. The voltage sensing apparatus of claim 6, wherein the reference potential is in a range from 0.3V to 1V.

11. The voltage sensing apparatus of claim 6, wherein the voltage supply of the amplifier circuit and the reference potential are different.

12. An amplification method, comprising:

processing an input signal using an input stage comprising a first set of transistors, the transistors of the first set comprising a semiconductor body;

processing the input signal from the input stage using a processing stage; and generating an output signal using the processing stage, wherein the processing stage comprises a second set of transistors, and wherein the transistors of the first set have a thicker gate oxide than the transistors of the second set, and wherein the transistors of the first set are suitable for higher voltage operation than the transistors of the second set;

supplying the first and second sets of transistors with a voltage supply; and connecting the semiconductor body of the first set of transistors to a reference potential to lower a threshold voltage of the first set of transistors, wherein the reference potential is connected to a reference input of the input stage via a high pass filter.

13. The method of claim 12, wherein the input signal is a differential input signal, and wherein processing the input signal using the input stage further comprises providing a first differential input to a gate of a first input transistor of the input stage, and providing a second differential input to a gate of a second input transistor of the input stage.

14. The method of claim 12, further comprising supplying the first and second sets of transistors with a voltage supply of less than 2V.

15. The method of claim 12, wherein the reference potential is in a range from 0.3V to 1V.

16. The method of claim 12, wherein the voltage supply of the first and second sets of transistors and the reference potential are different.

17. The amplifier circuit of claim 1, wherein the high-pass filter has a corner frequency of less than 10 Hz.

18. The method of claim 12, wherein the high-pass filter has a corner frequency of less than 10 Hz.

* * * * *